United States Patent [19]

Porter et al.

[11] Patent Number: 4,992,382

[45] Date of Patent: Feb. 12, 1991

[54] POROUS POLYMER FILM CALCIUM ION CHEMICAL SENSOR AND METHOD OF USING THE SAME

[75] Inventors: Marc D. Porter; Lai-Kwan Chau, both of Ames, Iowa

[73] Assignee: Iowa State University Research Foundation, Inc., Ames, Iowa

[21] Appl. No.: 396,446

[22] Filed: Aug. 21, 1989

[51] Int. Cl.$^5$ .................... G01N 33/20; G01N 21/00
[52] U.S. Cl. ......................... 436/79; 436/74; 422/55; 422/56
[58] Field of Search ............... 436/74, 76, 79; 422/55, 422/56, 57; 435/4

[56] References Cited

U.S. PATENT DOCUMENTS

| | | | |
|---|---|---|---|
| 2,583,890 | 1/1952 | Schwarzenbach | 436/79 X |
| 3,635,679 | 1/1972 | Bloch et al. | 422/55 X |
| 3,754,865 | 8/1973 | Gindler | 436/74 X |
| 3,798,000 | 3/1974 | Helger | 436/74 X |
| 4,083,972 | 4/1978 | Francis | 424/204 |
| 4,084,967 | 4/1978 | O'Brien | 96/29 R |
| 4,294,933 | 10/1981 | Kihara et al. | 521/27 |
| 4,405,574 | 9/1983 | Lee et al. | 423/157 |
| 4,522,951 | 6/1985 | Lee et al. | 521/28 |
| 4,594,225 | 6/1986 | Arai et al. | 436/79 X |
| 4,629,741 | 12/1986 | Beale, Jr. | 521/28 |
| 4,724,050 | 2/1988 | Bergeron et al. | 204/1 T |

FOREIGN PATENT DOCUMENTS 60-33049  2/1985  Japan .

OTHER PUBLICATIONS

Sigma Chemical Company, Biochemical and Organic Cpds for Research and Diagnostic Clinical Reagents, Price List, Feb. 1986, p. 299.

Primary Examiner—Robert J. Warden
Assistant Examiner—Thalia P. Vassilatos
Attorney, Agent, or Firm—Zarley, McKee, Thomte, Voorhees & Sease

[57] ABSTRACT

A method of measuring calcium ions is disclosed wherein a calcium sensitive reagent, calcichrome, is immobilized on a porour polymer film. The reaction of the calcium sensitive reagent to the Ca(II) is then measured and concentration determined as a function of the reaction.

18 Claims, 1 Drawing Sheet

4,992,382

POROUS POLYMER FILM CALCIUM ION CHEMICAL SENSOR AND METHOD OF USING THE SAME

The U.S. Government has certain rights in this invention pursuant to Contract Number W-7405-ENG-82, between the U.S. Department of Energy and Iowa State University.

BACKGROUND OF THE INVENTION

Chemical sensors are used to detect the presence of a metal cation in a substance and are useful in a variety of fields. Typically, a colorimetric reagent is immobilized on a support, such as optical fibers, and the sensor is applied in biomedical uses, process control, and environmental analysis. Detection of calcium ions (Ca(II)) is useful, for example, in detecting the amount of calcium in the blood of animals, or in detecting calcium in the food processing industry. The colorimetric reagent reacts with the calcium ion in a substance or solution so that there is a change in an optical property; for example, absorption, luminescence, or reflectance, and correlated with the concentration of the calcium ion. This is accomplished by correlating the concentration of the calcium ion to a calibration curve which relates the optical property to the concentration of the calcium.

Sensors which have been developed to this point have several deficiencies, including a slow response time because of barriers to mass transport at the polymer support, a low sensitivity due to weak analytical signal, a low selectivity due to interferences, and a long term instability because of degradation of the immobilized reagent or its desorptive loss from the support.

This invention relates to an improved sensor which provides for a rapid response time and high sensitivity through the use of a porous polymer film as the support material for the analytical reagent. High selectivity, and resistance to degradation are achieved by employing a calcium ion sensitive colorimetric reagent having sulfonic acid or carboxylic acid binding to the anion exchange polymer and calcium ion chelating groups.

A primary object of the invention is to provide for an improved chemical sensor of calcium ions in a solution or substance.

It is an objective of this invention to provide a chemical sensor for calcium ions which has a rapid response time.

A further object of the invention is to provide for a highly sensitive chemical sensor of calcium ions.

Yet a further object of the invention is to provide a chemical sensor with high selectivity for calcium ions.

Another object of the invention is to provide a chemical sensor which is resistant to degradation.

A still further object of the invention is to provide a chemical sensor in which the analytical reagent has strong binding to the underlying polymeric support.

Further objects of the invention will become apparent in the following disclosure.

SUMMARY OF THE INVENTION

A porous anion exchange polymer film is provided which has immobilized on it a calcium ion sensitive colorimetric reagent, preferably calcichrome. The reaction of the calcium ion analyte may be measured using the colorimetric reagent.

DETAILED DESCRIPTION OF THE INVENTION

Figure 1:
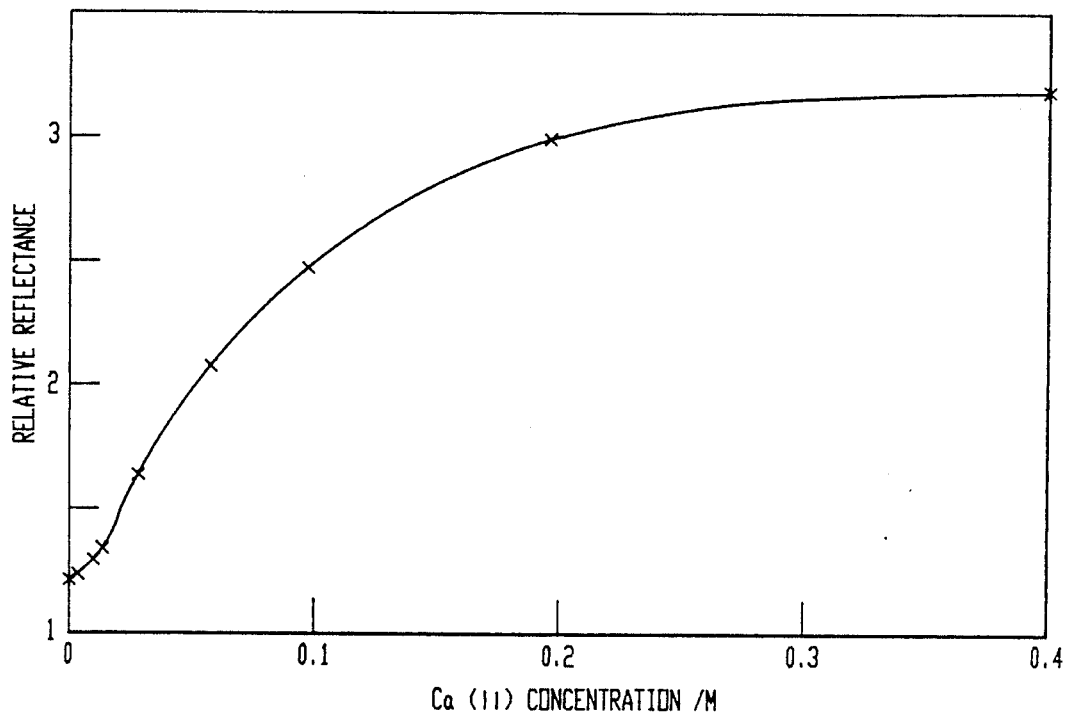
FIG. 1 is a graph with Ca(II) concentration as the x-axis and relative reflectance as the y-axis.

The anion exchange polymer film used in this invention is well known to those skilled in the art, however, a critical aspect is that the film must be porous. Enhanced porosity insures rapid response, and the large number of binding sites offered by a polymeric support provides a strong analytical signal. Such a porous anion exchange polymer film is available commercially and can be obtained, for example, from RAI Research Corporation in Hauppauge, N.Y., under the classification "N0030". Quaternized amines are used for this embodiment of the polymer film. The positive charge from the quaternized amines allows the calcichrome to stick to the film, and porosity assists in the improved response time. While quaternized amine polymers are preferred with the film, a polymer film which is permselective provides the desired properties. Such a film is permeable only to small molecules, and prohibits the permeation of macromolecules.

The degree of porosity will depend upon what is being analyzed. The film should be porous enough to allow the analyte, calcium, to pass through while preventing permeation of contaminants. In using the film for blood serum analysis, for example, the smallest degree of porosity preferred would be about 5,000 angstroms, and the largest 10 microns. The preferred range would be 0.5 microns up to 10 microns, with 10 microns the most preferred.

Immobilized on the film is a Ca(II) sensitive colorimetric reagent. Any agent with sulfonic acid or carboxylic acids that bind to the anion exchange polymer, and also contain Ca(II)-chelating groups provides the satisfactory response of the invention. However, it is necessary that the reagent retain its Ca(II)-chelating properties after being immobilized on the support. The effective reagent discovered in this invention is calcichrome, also referred to as calcion. Calcichrome is 2,8,8-trihydroxyl-1,1-azonaphthalene-3,6,3,6,tetrasulfonicacid. Calcichrome is applied to the support in a concentration of $5 \times 10^{-4}$ mM/g to $2 \times 10^{-2}$ mM/g of dry films. The preferred concentration is $1 \times 10^{-2}$ mM/g of dry film.

Several methods are available for trapping the reagent on the film and include covalent binding, electrostatic binding, adsorption, or trapping the analyte in a solution reservoir behind a membrane. With electrostatic binding calcichrome negative charges are attracted to the amine positive charges. In adsorption, a strong chemical bond is not employed, but a variety of interactions retain the reagent on the film. The calcichrome can be trapped behind a membrane, such as Teflon or cellulose, so that the calcium can diffuse through and react with the calcichrome. The specific method employed for trapping the reagent is not critical.

If impregnating the calcichrome onto the film, the timing is not critical, and satisfactory results are obtained when a time period from about five minutes to overnight is employed. Optionally, the film may be air-dried for storage or used immediately. When used in the optical sensing of Ca(II), it is preferable that the sample solution be at or about pH 12.

Once the calcichrome is immobilized on the film, the optical and/or chemical properties of the sensor are then evaluated as the function of the Ca(II). An example of a method of evaluating such properties is through the use of diffuse reflectance spectroscopy. A standard is used to which the results may be compared in order to determine the concentration of the Ca(II).

By using the invention disclosed, it is possible to obtain a reaction time in a much shorter time period than is obtained with other methods. Usually, with present methods, one must wait five to ten minutes in order to get a reaction. Here, the results are obtained in far less than one minute and can be obtained in as short a time as fifteen seconds or less.

The following is presented as a means of illustrating the invention, and is not intended to limit the process. Variations will be evident to one skilled in the art as falling within the scope of the invention.

EXAMPLE

Calcichrome, obtained as its tetra-sodium salt (Pfalz & Bauer, Inc., Waterbury, Conn.) was immobilized at the porous anion exchange polymer film (RAI Research Corporation, Hauppauge, N.Y.) by immersing a film in an aqueous calcichrome solution at room temperature for several hours. After removal from the solution, excess reagent was washed from the substrate with deionized water.

Both optode and flow cell for the chemical sensor were constructed to use in testing the chemical sensor feasibility. Optical fibers (400 m diameter, Ensign-Bickford Optics Co., Avon, Conn.) were used as light transmission lines in both designs. Incoming light was transmitted by the first array of optical fibers and the diffused reflected light at the sensor film was collected by the second array of optical fibers and transmitted to a monochromator. A Xenon arc lamp (Oriel Corporation, Stanford, Conn.) was used as a light source; the transmitted radiation was dispersed with a 0.22 m grating monochromator and monitored with a digital photometer (Spex DPC-2, SPEX, Inc., Edison, N.J.) which was operated in an analog mode.

The optical response of calcichrome immobilized at a porous anion exchange polymer film in the absence or in the presence of Ca(II) of pH 12.1 was then determined. The resulting calibration curve plotting relative reflectance to Ca(II) concentrations is shown in FIG. 1. This enabled the concentration of Ca(II) to be determined. The limit of detection of the sensor obtained under the stated conditions is in the order of mM. The transient optical response of the sensor was measured by injecting a Ca(II) solution at pH 12.1 through the flow cell. Equilibration (99% completion) was achieved in about 13 seconds; the response reaches 63% (1-1/e) of its maximum reflectance value in about 3.7 seconds.

The stability of the sensor response was examined by measuring the diffuse reflected light intensity before and after prolonged exposure of incident light, and between successive days. No significant difference in intensity was observed.

The interferences of other metal ions were examined using Mg(II), Ba(II) and Sr(II) as the test ions. The optical response was measured in pH 12.1 buffer and in saturated solutions of these ions at pH 12.1. The reflectance spectra obtained were almost indistinguishable.

Thus it can be seen that the invention accomplishes at least all of its objectives.

We claim:

1. A method of measuring calcium in a solution comprising:
   immobilizing a calcium sensitive reagent having an acid selected from the group consisting of sulfonic acid and carboxylic acid and having calcium chelating groups on porous polymer film the acid capable of binding to the film and the calcium chelating groups retaining chelating properties after immobilization;
   contacting said film with said calcium containing solution;
   measuring reaction of said calcium sensitive reagent to said calcium containing solution; and
   determining calcium concentration in said solution as a function of said reaction of the calcium sensitive reagent.

2. The method of claim 2 wherein said calcium sensitive reagent is immobilized on said film by electrostatic binding.

3. The method of claim 1 wherein said calcium sensitive reagent reaction is measured by diffuse reflectance spectroscopy.

4. The method of claim 1 wherein said reagent is immobilized on a film having a porosity to allow said calcium in said solution to permeate said film while prohibiting permeation of other macromolecules.

5. The method of claim 1 wherein said method is used for blood serum analysis and said reagent is immobilized on a film having a porosity of about 5,000 angstroms up to about 10 microns.

6. The method of claim 1 wherein calcichrome is used as said calcium sensitive reagent.

7. The method of claim 3 wherein said calcichrome is concentrated on said film at $5 \times 10^{-4}$ mM/g to $2 \times 10^{-2}$ mM/g.

8. A method of measuring calcium in a solution comprising:
   immobilizing a calcium sensitive reagent on a porous polymer film containing quarternized amine;
   contacting said film with said calcium containing solution;
   measuring reaction of said calcium sensitive reagent to said calcium containing solution; and
   determining calcium concentration in said solution as a function of said reaction of the calcium sensitive reagent.

9. A method of measuring calcium in a solution comprising:
   immobilizing a calcium sensitive reagent on porous polymer film;
   contacting said film with said calcium containing solution;
   measuring reaction of said calcium sensitive reagent to said calcium containing solution;
   determining calcium concentration in said solution as a function of said reaction of said calcium sensitive reagent,
   wherein said calcium concentration may be determined in up to one minute.

10. A sensor for measuring the concentration of calcium in a solution comprising a porous polymer film having a calcium sensitive reagent immobilized thereon, the reagent comprising an acid selected from the group consisting of sulfonic acid and carboxylic acid capable of binding to said polymer film and having calcium chelating groups capable of retaining the chelating property after immobilization.

11. The sensor of claim 10 wherein said film has a porosity to allow said calcium in said solution to permeate said film while prohibiting permeation of other macromolecules.

12. The sensor of claim 10 wherein said sensor measures said concentration of calcium in up to one minute.

13. The sensor of claim 10 wherein said film has a porosity of about 5,000 angstroms up to about 10 microns.

14. The sensor of claim 13 wherein said film has a porosity of about 0.5 microns up to about 10 microns.

15. The sensor of claim 10 wherein said calcium sensitive reagent is calcichrome.

16. The sensor of claim 15 wherein said film contains calcichrome at a concentration of $5 \times 10^{-4}$ mM/g to $2 \times 10^{-2}$ mM/g.

17. The sensor of claim 16 wherein said film contains calcichrome at a concentration of $1 \times 10^{-2}$ mM/g.

18. A sensor for measuring a concentration of calcium in a solution comprising a porous polymer film having a calcium sensitive reagent immobilized thereon, said porous polymer film containing quaternized amine.

* * * * *